United States Patent
Wooley et al.

(10) Patent No.: US 9,828,317 B2
(45) Date of Patent: Nov. 28, 2017

(54) METHOD FOR PURIFICATION OF ALCOHOLS

(71) Applicant: GEVO, Inc., Englewood, CO (US)

(72) Inventors: Robert Wooley, Englewood, CO (US); Steven Lythgoe, Englewood, CO (US); Jose Guimaraes, Englewood, CO (US); Michael McIntyre, Englewood, CO (US); Lanny Robbins, Englewood, CO (US)

(73) Assignee: Gevo, Inc., Englewood, CO (US)

( * ) Notice: Subject to any disclaimer, the term of this patent is extended or adjusted under 35 U.S.C. 154(b) by 463 days.

(21) Appl. No.: 14/411,832

(22) PCT Filed: Jun. 28, 2013

(86) PCT No.: PCT/US2013/048460
§ 371 (c)(1),
(2) Date: Dec. 29, 2014

(87) PCT Pub. No.: WO2014/004966
PCT Pub. Date: Jan. 3, 2014

(65) Prior Publication Data
US 2015/0166444 A1    Jun. 18, 2015

Related U.S. Application Data

(60) Provisional application No. 61/666,648, filed on Jun. 29, 2012.

(51) Int. Cl.
*C07C 29/80* (2006.01)
*B01D 3/00* (2006.01)
*B01D 3/26* (2006.01)
*C07C 29/82* (2006.01)
*B01D 3/14* (2006.01)

(52) U.S. Cl.
CPC ............. *C07C 29/80* (2013.01); *B01D 3/002* (2013.01); *B01D 3/143* (2013.01); *C07C 29/82* (2013.01); *Y10T 29/49716* (2015.01)

(58) Field of Classification Search
CPC ........ B01D 3/002; B01D 3/143; C07C 29/80; C07C 29/82
See application file for complete search history.

(56) References Cited

U.S. PATENT DOCUMENTS

| | | |
|---|---|---|
| 5,417,813 A | 5/1995 | Berg |
| 2007/0144886 A1 | 6/2007 | Sylvester et al. |
| 2011/0087000 A1 | 4/2011 | Peters et al. |
| 2011/0124068 A1 | 5/2011 | Evanko et al. |
| 2011/0303526 A1 | 12/2011 | Lee et al. |

FOREIGN PATENT DOCUMENTS

CN    1013677110 A    2/2009

OTHER PUBLICATIONS

International Search Report, PCT appl. No. PCT/US2013/048460, 4 pages (dated Feb. 14, 2014).
Written Opinion of the International Searching Authority, PCT appl. No. PCT/US2013/048460, 15 pages (dated Feb. 14, 2014).

*Primary Examiner* — Renee Robinson
*Assistant Examiner* — Derek Mueller
(74) *Attorney, Agent, or Firm* — Cooley LLP (57) ABSTRACT

This invention is directed to methods for recovery of C3-C6 alcohols. The recovery process advantageously utilizes the immiscible properties of a first phase liquid and a second phase liquid to separate the liquids prior to processing C3-C6 alcohols to recovery. The invention is also directed to C3-C6 alcohol-containing compositions.

21 Claims, 3 Drawing Sheets

METHOD FOR PURIFICATION OF ALCOHOLS

FIELD OF THE INVENTION

This application relates generally to methods for recovery and purification of C3-C6 alcohols.

BACKGROUND

Alcohols, including higher molecular weight alcohols having from three to six carbon atoms, can be produced industrially by a variety of processes. Some processes include the production of such alcohols by fermentation, e.g., by microorganisms that make the alcohols through metabolic processes. A challenge for the successful industrial production of such alcohols, in addition to producing them in commercially relevant quantities, is the recovery and purification of the alcohols from solutions in which the alcohols are very dilute, such as fermentation broths. For example, butanol produced by fermentation can be in solutions at concentrations on the order of just a few weight percent (e.g., from about 0.5 wt. % to about 10 wt. %).

Methods for the recovery of alcohols from fermentation broths have been described. For example, U.S. Pat. No. 8,101,808 and United States Patent Publication No. 20110124068 disclose exemplary processes for recovery of alcohols from fermentation broths.

Alcohols can be used in a variety of practical applications. For example, some alcohols such as ethanol and butanol can be used as biofuels, typically as an additive in combination with other fuels (e.g., gasoline). There are other uses of industrial alcohols as well, including use as solvents, or as precursors for the production of higher molecular weight compounds. However, different applications for the use of such alcohols have different purity requirements for the alcohol product(s). A variety of factors can affect the utility of any given recovery and purification process, including its recovery efficiency, as well as capital, operating and maintenance costs. Accordingly, there is a need for processes for the recovery and purification of such alcohols that are cost-effective and efficient, and that allow for the production of alcohols at levels of purity that are appropriate for an intended application.

SUMMARY

One embodiment of the present invention is a method to recover a C3-C6 alcohol from a stream, which can be a part of a fermentation broth, that includes a C3-C6 alcohol, ethanol and water in a recovery system. The method includes separating a water-rich liquid phase from a C3-C6 alcohol-rich liquid phase, and conducting the water-rich liquid phase to a column to produce a vapor stream that includes water and ethanol. The vapor stream is conducted to a rectification column to produce a liquid distillate comprising water and ethanol, and the liquid distillate is not reintroduced to the recovery system. The method further includes recovering C3-C6 alcohol from the alcohol-rich liquid phase. In this embodiment, the vapor stream can be enriched in low molecular weight alcohols, which can include C2 and C3 alcohols. This embodiment can also include conducting the C3-C6 alcohol-rich liquid phase to a dehydration column to dehydrate the C3-C6 alcohol and produce a C3-C6 dehydrated alcohol which can include less than about 1 wt. % water and greater than about 96 wt. % of a single C3-C6 alcohol. The dehydrated alcohol can be conducted to a purification column to purify the C3-C6 alcohol to solvent grade C3-C6 alcohol which can include greater than about 99.1 wt. % of a single C3-C6 alcohol.

This embodiment can also include conducting a bottom liquid produced in the rectification column to a distillation column to remove ethanol and produce a distilled bottom liquid, and conducting the distilled bottom liquid to the step of separating a water-rich liquid phase from a C3-C6 alcohol-rich liquid phase. This embodiment can also include sub-cooling a vapor distillate produced in the rectification column to recover a substantial portion of the vapor distillate and recycle the substantial portion of the vapor distillate to the recovery system.

This embodiment of the invention can be conducted in a retrofit ethanol production plant that includes an ethanol recovery system comprising a stripping column. In this embodiment, the column in which a vapor stream is produced can be the column from the ethanol recovery system, which can also be a first partition portion of a column from the ethanol recovery system. The C3-C6 recovery system can also include a dehydration column which can be a retrofit rectification column of the ethanol recovery system, such as a second partition portion of the column from the ethanol recovery system. The method to recover a C3-C6 alcohol in the retrofit ethanol production plant cannot require or use a molecular sieve.

In all embodiments of the invention, the C3-C6 alcohol can be propanol, butanol, pentanol, hexanol or a mixture thereof. If the alcohol is propanol, it can be selected from 1-propanol and 2-propanol. If the alcohol is butanol, it can be selected from 1-butanol, 2-butanol, tert-butanol (2-methyl-2propanol), and isobutanol (2-methyl-1-propanol). If the alcohol is pentanol, it can be selected from 1-pentanol, 2-pentanol, 3-pentanol, 2-methyl-1-butanol, 3-methyl-1-butanol, 2-methyl-2-butanol 3-methyl-2-butanol, and 2,2-dimethyl-1-propanol. If the alcohol is hexanol, it can be selected from 1-hexanol, 2-hexanol, 3-hexanol, 2-methyl-1-pentanol, 3-methyl-1-pentanol, methyl-1-pentanol, 2-methyl-2-pentanol, 2-methyl-2-pentanol, 4-methyl-2-pentanol, 2-methyl-3-pentanol, 3-methyl-3-pentanol, 3,3-dimethyl-1-butanol, 2,2-dimethyl-1-butanol, 2,3-dimethyl-1-butanol, 2,3-dimethyl-2-butanol, 3,3-dimethyl-2-butanol, and 2 ethyl-1-butanol.

Another embodiment of the present invention is a method to recover a C3-C6 alcohol from a stream including a C3-C6 alcohol and water in a recovery system. The method includes separating a water-rich liquid phase from an alcohol-rich liquid phase, and conducting the alcohol-rich liquid phase to a dehydration column to produce a bottoms fraction that includes more than about 96 wt. % of a single C3-C6 alcohol. This method can also include conducting a vapor distillate from the dehydration column to a condenser to produce a liquid including the single C3-C6 alcohol and a vapor stream of non-condensable fluids (i.e., gases). This method can alternatively include conducting the bottoms fraction to a purification column to produce a purified distillate with more than about 99.1 wt. % C3-C6 alcohol. This method can also include conducting a vapor stream with the C3-C6 alcohol and water to a flash drum to produce a vapor fluid stream including an uncondensable gas, the C3-C6 alcohol, water and ethanol. The vapor fluid stream is condensed and the condensed portion of the vapor stream is recycled to the recovery system. This embodiment can also include conducting the bottoms fraction to a purification column to produce a purified liquid distillate having greater than about 99.1 wt. % C3-C6 alcohol. In a further alternative, the method includes removing a product side stream from the dehydration column and/or removing a product side stream from the purification column.

A further embodiment of the present invention is a composition that includes at least about 94 wt. % butanol and at least about 1.5 wt. % pentanol. The composition can alternatively include at least about 96 wt. % butanol and/or at least about 1.5 wt. % pentanol. Also, the composition can have less than about 2 wt. % or 1 wt. % water. The pentanol can be 2-methyl-1-butanol, 3-methyl-1-butanol and combinations thereof, and the butanol can be a renewable butanol which can be 1-butanol, 2-butanol, tert-butanol (2-methyl-2-propanol), or isobutanol (2-methyl-1-propanol), and preferably is isobutanol (2-methyl-1-propanol).

Another embodiment of the invention is a composition that includes at least about 99.1 wt. % butanol and a C3-C6 alcohol other than butanol in an amount less than 0.5 wt. %. The C3-C6 alcohol can be propanol, pentanol, or hexanol.

A further embodiment of the present invention is a method to recover a C3-C6 alcohol from a stream that includes a C3-C6 alcohol and water in a recovery system. This embodiment includes separating a water-rich liquid phase from a C3-C6 alcohol-rich liquid phase, and conducting the water-rich liquid phase to a first stripper section of a column to remove a vapor stream including C3-C6 alcohol, ethanol and water from the water-rich liquid phase. The method further includes conducting the alcohol-rich liquid phase to a second dehydration section of the column to remove water from the C3-C6 alcohol-rich liquid phase. In this method, the column can be a partitioned stripper column from an ethanol production plant. Further, in this method, an overhead of the first stripper section can be fed to a rectification column to remove water and ethanol from the vapor stream.

The present invention also includes as an embodiment, a method to retrofit an ethanol production plant by partitioning a stripper column from the ethanol production plant to a dual function column. In this method, the column includes an inlet for a water-rich liquid phase and a first stripper section of the column to remove a vapor stream comprising C3-C6 alcohol, ethanol and water from the water-rich liquid phase. The column also includes an inlet for a C3-C6 alcohol-rich liquid phase and a second dehydrator section of the column to remove water from the C3-C6 alcohol-rich liquid phase.

A further embodiment of the present invention is a dual function column for recovery of C3-C6 alcohol. The column includes an inlet for a water-rich liquid phase and a first stripper section of a column to remove a vapor stream comprising C3-C6 alcohol, water and ethanol from the water-rich liquid phase. The column also includes an inlet for a C3-C6 alcohol-rich liquid phase and a second dehydrator section of the column to remove water from the C3-C6 alcohol-rich liquid phase.

Another embodiment of the invention is a composition that includes at least about 94 wt. % isobutanol and less than about 2 wt. % water. The composition further includes an impurity selected from acetaldehyde, acetic acid, ethanol, lactic acid, 1-propanol, glycerol, isobutylaldehyde, isobutyric acid, 1-butanol, 2,3-butanediol, 2-methyl-1-butanol, 3-methyl-1-5 butanol, isobutyl acetate, 2-phenylethanol and combinations thereof, and the impurity is less than about 6 wt. % of the composition. This composition can include at least about 96 wt. % isobutanol, less than about 1 wt. % water and an impurity selected from acetic acid, ethanol, lactic acid, 1-propanol, isobutyric acid, 1-butanol, 2,3-butanediol, 2-methyl-1-butanol, 3-methyl-1-butanol, isobutyl acetate, 2-phenylethanol and combinations thereof, wherein the impurity is less than about 4 wt. % of the composition.

A further embodiment of the invention is a composition that includes greater than about 99.2 wt. % isobutanol and less than about 0.25 wt. % water. The composition further includes an impurity selected from acetaldehyde, acetic acid, ethanol, lactic acid, 1-propanol, glycerol, isobutylaldehyde, isobutyric acid, 1-butanol, 2,3-butanediol, 2-methyl-1-butanol, 3-methyl-1-butanol, isobutyl acetate, 2-phenylethanol and combinations thereof, and the impurity is less than about 0.8 wt. % of the composition. This composition can also include more than about 99.5 wt. % isobutanol, less than about 0.1 wt. % water and an impurity selected from ethanol, 1-propanol, 1-butanol, 2-methyl-1-butanol, 3-methyl-1-butanol, isobutyl acetate and combinations thereof, wherein the impurity is less than about 0.5 wt. % of the composition.

DETAILED DESCRIPTION

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

Throughout the present specification, the words "a" or "an" are understood to mean "one or more" unless explicitly stated otherwise. Further, the words "a" or "an" and the phrase "one or more" may be used interchangeably.

The present disclosure describes methods to recover and purify one or more C3-C6 alcohols from, e.g., a feed stream that comprises two or more components. At least one component of the feed stream is not completely miscible in one of the other components. The recovery of C3-C6 alcohol(s) from the feed stream results in the concentration or purification of the C3-C6 alcohol(s) by the separation and/or removal of the other components in the feed stream. For example, in the case of isobutanol, a C3-C6 alcohol, the solubility limit of isobutanol in water at about 25° C. is about 2.4 mol % and the solubility limit of water in isobutanol at about 25° C. is about 46.3 mol %. Thus, an isobutanol-water mixture can form a single liquid phase, or two liquid phases, depending on the relative concentrations of isobutanol and water. A feed stream that has a concentration which falls in the two-phase regime will form two liquid phases, a bottom, higher density phase which is water-rich (i.e., a water-rich liquid phase) and a top, lower density phase which is isobutanol-rich (i.e., an isobutanol-rich liquid phase). The C3-C6 alcohol-rich liquid phase can be refined in order to create a purified C3-C6 alcohol.

In one embodiment, the present invention includes a method to recover a C3-C6 alcohol from a feed stream comprising C3-C6 alcohol, ethanol and water in a recovery system. The method includes separating a water-rich liquid phase from a C3-C6 alcohol-rich liquid phase. The water-rich liquid phase is conducted to a stripping column to produce an overhead vapor stream comprising a C3-C6 alcohol, water and ethanol. The vapor stream is conducted to a rectification column to produce a liquid distillate comprised primarily of water and ethanol. The liquid distillate is not reintroduced to the recovery system. The bottoms from the rectification column are recycled to the recovery system. A C3-C6 alcohol is recovered from the alcohol-rich phase. The term stripping column generally refers to a column in which lower boiling components of a liquid stream are volatilized to be removed from the stream. The term rectification column generally refers to a column in which lower boiling components of a liquid stream are volatilized and brought into countercurrent contact with a falling liquid stream. In embodiments wherein the liquid stream comprises one or more alcohols which are not miscible with water in all proportions, the resulting mixture in the rectification column can include a vapor stream and a two phase liquid composition.

Reference to a recovery system can be to process and equipment that is used for recovery of a product (e.g., a C3-C6 alcohol). Processes which can be employed in for recovery of a product include distillation, liquid-liquid extraction, absorption, adsorption, membrane separation (e.g., reverse osmosis, pervaporation, etc.) and decantation. As will be appreciated, when products are recovered, any one process step is typically not 100% efficient and therefore, often, a waste stream will be recycled back into a process for recovery of residual product amounts in the waste stream. In some embodiments, a recovery system is a system for recovery of products and handling concentrated streams that are downstream from a primary recovery or purification step. For example, a primary recovery or purification step is one in which, in the instance of biological production of a C3-C6 alcohol, a stream comprising whole fermentation broth is first treated to recover or concentrate the C3-C6 alcohol. In this instance, the streams of the recovery system are not mixed or combined with or in the streams in the primary recovery or purification step in which, for example, a whole fermentation broth is processed. In other words, in some embodiments of the present invention, the term recovery system does not include a primary recovery or purification step and/or the recovery system does not include streams that intermingle with a primary recovery or purification step. Such embodiments have the advantage of the recovery system not having to handle a more dilute stream, e.g., a fermentation broth, but rather a more concentrated incoming stream from one or more primary recovery or purification steps.

In various embodiments, a feed stream is provided to the recovery system. In some embodiments, the feed stream can be a portion of a fermentation broth. The feed stream can be produced using methods described in U.S. Pat. No. 8,101,808, or U.S. Publication No. 20110124068, which are incorporated in their entirety by reference. The methods of the present invention are suitable for use with any feed stream derived from a fermentation broth. Suitable fermentation processes include the use of conventional fermentation substrates such as corn, but also include the use of cellulosic substrates that can be processed or pretreated (e.g., by enzymatic, thermal or chemical treatment of cellulosic materials) to provide fermentable sugars for use as substrates by microorganisms. For example, as described in detail in U.S. Pat. No. 8,101,808, a feed stream for the present invention can be produced by increasing the concentration of a C3-C6 alcohol in a portion of the fermentation broth to form a C3-C6 alcohol-rich liquid phase and a water-rich liquid phase from the portion of the fermentation broth.

In one embodiment in which the step of increasing the concentration of the C3-C6 alcohol comprises distilling a vapor phase comprising water and the C3-C6 alcohol and condensing the vapor phase, the method can also include treating the C3-C6 alcohol-rich phase for water removal. The step of treating can include selective removal of water, selective binding of water or selective rejection of water. Alternatively, the step of treating can include addition of a hydrophilic solute, addition of a carbon source, reverse osmosis, dialysis, adsorption of the butanol on a selective adsorbent, extraction of the butanol into a selective extractant, adsorption of water on a selective adsorbent, or extraction of water into a selective extractant.

In one embodiment, the step of distilling is conducted in a flash tank, that can be operatively connected to a fermentation vessel, and the process can further comprise circulating the fermentation broth from the fermentation vessel to the flash tank, evaporating at least a portion of the fermentation broth, and circulating the remaining fermentation broth from the flash tank to the fermentation vessel. A "flash" distillation is a one stage distillation conducted in a flash tank or flash vessel, wherein the vapor and liquid outlet streams from the flash tank are in equilibrium with each other and the temperature and pressure of each phase is substantially the same. Multistage distillation, on the other hand, comprises a series of two or more "stages" in a single distillation vessel (e.g., a distillation column). Thus, during distillation in, e.g., a multi-stage distillation system, such as a distillation column, a vapor exiting the top of the distillation vessel and the liquid exiting the bottom of the distillation vessel typically leave at different temperatures and pressures.

According to another embodiment, the present process includes reducing the pressure in a distillation vessel relative to the pressure in the fermentation vessel. Such a pressure reduction allows for vaporization of a stream in a flash distillation process at lower temperatures. Alternatively or in addition, the process can include increasing pressure on the aqueous solution from the distillation vessel in the fermentation vessel. Such a pressure increase heats the compressed stream, and the heated stream can be used to preheat other streams in the system at various points by, e.g., passing the streams through a heat exchanger. For example, the heat from the compressed stream can be used to preheat a feed to a flash tank, to a beer still and/or to a distillation column, and can also be used in on or more evaporators used to concentrate thin stillage to syrup. These components are discussed in detail below.

Flash tank vacuum evaporation operations have less engineering concerns with respect to pressure drop under vacuum because the flash tank is a single stage separation without additional stages which may result in a pressure drop over two or more stages. Accordingly, the differential pressure across flash tank operations (i.e., between a vapor exit stream and a liquid exit stream) can be very low. Design calculations for vapor generation in the flash tank and sizing of piping systems can be appropriately selected to achieve low pressure drop. The distillation of a C3-C6 alcohol in a flash tank requires less vacuum than a distillation column and, thus, the flash tank has lower operating cost and capital costs (e.g., the equipment can be smaller in size, simpler in design and/or have lower capital cost).

In one embodiment, when the step of increasing the concentration of the C3-C6 alcohol comprises distilling a vapor phase comprising water and the C3-C6 alcohol, the mixed vapor can include an azeotropic composition of the C3-C6 alcohol and water. An azeotrope is a mixture of chemical components that has identical compositions of the liquid and vapor phases in equilibrium with each other. This azeotropic phenomenon occurs because of molecular interactions between different chemical components. Azeotropes are generally viewed as a limitation in chemical separations because the azeotrope composition "pinch point" prevents the distillation of the mixture into its pure components. Instead of producing pure components from the distillation process, the azeotrope distills at the azeotropic composition at the top of the distillation column, in the case of a minimum boiling point azeotrope, or from the bottom of the distillation column, in the case of a maximum boiling point azeotrope.

The formation of C3-C6 alcohol-rich and water-rich liquid phases from a feed stream can be accomplished by a variety of methods. The step of forming the two liquid phases can be active. For example, in some embodiments, the step of forming can comprise condensing a distilled vapor phase that forms two liquid phases after condensation (e.g., as described herein for water/isobutanol mixtures). Alternatively or in addition, chilling or cooling the treated portion of the aqueous solution can result in the formation of the two liquid phases. Other steps for actively forming the two liquid phases can include using equipment shaped to promote the separation of phases. Separation of the liquid phases can be accomplished in various unit operations including liquid-liquid separators comprising a liquid/liquid separator utilizing specific gravity differences between the phases and a water boot, g-force separation as in a centrifuge, or centrifugal liquid-liquid separators. Also suitable are settlers such as mixer-settler units used in solvent extraction processes. In some embodiments the step of forming is passive and can simply be a natural consequence of the step of increasing the concentration of the C3-C6 alcohol. Alternatively, compositions can be treated or processed to achieve or enhance formation of phases. For example, as illustrated in Examples 1-19 of U.S. Pat. No. 8,101,808, the formation of two liquid phases with C3-C6 alcohols can be accomplished by, inter alia, addition of solvents, sugar, salts, and hydrophilic compounds.

A water-rich liquid phase can be separated from a C3-C6 alcohol-rich phase using any suitable method and device. Separating a water-rich liquid phase from an alcohol-rich liquid phase refers to physical separation of the two liquid phases, and can include removing, skimming, pouring out, decanting or otherwise separating one liquid phase from another and can be accomplished by any means known in the art for separation of liquid phases. As used herein, any suitable liquid-liquid separator can be used. In some embodiments, at least one liquid-liquid separator can be used. In some embodiments, extraction processes can be used.

The terms "a water-rich liquid phase" and "a C3-C6 alcohol-rich liquid phase" can refer to streams that result from a purification step in which the C3-C6 alcohol in a feed stream is concentrated in a C3-C6 alcohol-rich liquid phase, as compared to a water-rich liquid phase from which the C3-C6 alcohol was removed or concentrated. Thus, in general, a C3-C6 alcohol-rich liquid phase refers to a composition that has a C3-C6 alcohol concentration that is greater than the C3-C6 alcohol concentration in a corresponding water-rich liquid phase. Likewise, a water-rich liquid phase refers to a composition that has a water concentration that is greater than the water concentration in a corresponding C3-C6 alcohol-rich liquid phase. In addition to water and C3-C6 alcohol, the liquid phases (e.g., either a water-rich liquid phase, a C3-C6 alcohol-rich liquid phase, or both) can include a variety of impurities, including without limitation, other alcohols, organic acids, dissolved gases, fermentation byproducts, 2,3-butanediol, 3-methyl-1-butanol, 2-methyl-1-butanol, isobutyl acetate, 2-phenylethanol, carbon dioxide, ammonia, acetaldehyde and acetic acid and combinations thereof.

In certain embodiments, the alcohol-rich liquid phase typically comprises a C3-C6 alcohol, water and can also include ethanol. In some embodiments, the alcohol-rich liquid phase can comprise greater than about 50 wt. % of the C3-C6 alcohol, greater than about 55 wt. %, greater than about 60 wt. %, greater than about 65 wt. %, greater than about 70 wt. %, greater than about 75 wt. %, or greater than about 76 wt. %. The alcohol-rich liquid phase can comprise water in an amount less than about 25 wt. % water, less than about 20 wt. %, less than about 15 wt. %, less than about 10 wt. %, or less than about 5 wt. %. In embodiments that further comprise ethanol, the alcohol-rich liquid phase can comprise ethanol in an amount less than about 7 wt. % ethanol, or less than about 4 wt. %.

In certain embodiments, the water-rich liquid phase typically comprises C3-C6 alcohol, water and ethanol. In some embodiments, the water-rich liquid phase can comprise greater than about 50 wt. % water, greater than about 55 wt. % water, greater than about 60 wt. % water, greater than about 65 wt. % water, greater than about 70 wt. % water, greater than about 75 wt. % water, greater than about 80 wt. % water, greater than about 85 wt. % water, greater than about 90 wt. % water, or greater than about 93 wt. %. In other embodiments, the water-rich liquid phase can comprise less than about 4 wt. % C3-C6 alcohol, less than about 5 wt. %, less than about 6 wt. %, or less than about 7 wt. %. In some embodiments, the water-rich liquid phase can comprise greater than about 0.5 wt. % ethanol, greater than about 0.8 wt. %, greater than about 0.9 wt. %, greater than about 1 wt. %, greater than about 1.2 wt. %, or greater than about 2 wt. %.

Ethanol can be present in the feed stream, e.g., as an impurity from a previous process or as a component used in a previous process. In some embodiments, the feed stream is a portion of a fermentation broth. In some fermentation processes, ethanol can be added to the broth as a nutritional requirement in the fermentation, and in some fermentation processes, ethanol can be present as a by-product or as an impurity produced from a contaminating microorganism, such as a wild-type yeast. While ethanol can be beneficial or acceptable in the fermentation process, it will typically be considered to be an impurity in the recovery process of a C3-C6 alcohol. Thus, the method for recovering a C3-C6 alcohol described herein advantageously removes a stream containing ethanol from the recovery system.

This embodiment further includes conducting the water-rich liquid phase to a stripping column to produce a vapor stream that includes water and ethanol. The vapor stream can also include C3-C6 alcohol and can be enriched in low molecular weight alcohols such as C2 and/or C3 alcohols. As used herein, reference to a stream being enriched with respect to one or more components means that the resulting stream, such as a vapor stream in a distillation, has a greater concentration of the one or more components relative to the incoming stream. In some embodiments, the vapor stream composition can comprise greater than about 40 wt. % water, greater than about 45 wt. %, greater than about 50 wt. % water, greater than about 52 wt. % water or greater than about 55 wt. % water. In some embodiment, the vapor stream composition can comprise greater than about 2 wt. % ethanol, greater than about 4 wt. % ethanol, greater than about 6 wt. % ethanol or greater than about 8 wt. % ethanol. The vapor stream can also comprise a C3-C6 alcohol. In such embodiments, the vapor stream composition can comprise greater than 20 wt. % C3-C6 alcohol, greater than about 25 wt. % C3-C6 alcohol, greater than about 30 wt. % C3-C6 alcohol, greater than about 35 wt. % C3-C6 alcohol or greater than about 40 wt. % C3-C6 alcohol. In other embodiments, the vapor stream can comprise between about 40 wt. % and about 65 wt. % water, between about 45 wt. % and about 60 wt. % water, or between about 50 wt. % and about 55 wt. % water. In still other embodiments, the vapor stream can comprise between about 2 wt. % and about 15 wt. % ethanol, between about 3 wt. % and about 12 wt. % ethanol, or between about 5 wt. % and about 10 wt. % ethanol. In still other embodiments, the vapor stream can comprise between about 20 wt. % and about 60 wt. % C3-C6 alcohol, between about 30 wt. % and about 50 wt. % C3-C6 alcohol, or between about 35 wt. % and about 45 wt. % C3-C6 alcohol.

A bottoms stream is also produced in the stripping column. In some embodiments, the bottoms stream composition can comprise greater than about 80 wt. % water, greater than about 85 wt. % water, greater than about 90 wt. % water, greater than about 95 wt. % water, or greater than about 99 wt. %. The bottoms stream composition can comprise less than about 2 wt. % ethanol, less than about 1 wt. % ethanol, less than about 0.5 wt. % ethanol or less than about 0.3 wt. % ethanol. The bottoms stream composition can comprise less than about 1 wt. % C3-C6 alcohol, less than about 0.5 wt. % C3-C6 alcohol, less than about 0.1 wt. % C3-C6 alcohol, less than about 0.05 wt. % C3-C6 alcohol or less than about 0.02 wt. % C3-C6 alcohol.

As used herein, the stripping column can be any suitable device. In some embodiments, the column can be a distillation column, a packed column with a variety of different packings, or a trayed column with a variety of tray types and/or configurations.

In certain embodiments, the only stream entering the stripping column is a water-rich liquid phase, and no other sources of water. C3-C6 alcohol or ethanol are introduced into the stripping column. For example, in one embodiment, the stripping column does not have more than the single incoming water-rich liquid phase. In one embodiment, the stripping column does not have whole fermentation broth as an incoming stream.

Some embodiments further include conducting the vapor stream from a stripping column to a rectification column to produce a liquid distillate that includes water and ethanol. The rectification column can produce a vapor that includes a C3-C6 alcohol, water and ethanol, that can be condensed in a condenser to form a liquid distillate. Remaining portions of the vapor that are not condensed to form the liquid distillate can be processed as discussed herein. The liquid distillate can be removed from the rectification column and not reintroduced to the recovery system. In some embodiments, the liquid distillate composition can comprise greater than about 50 wt. % ethanol, greater than about 55 wt. % ethanol, greater than about 60 wt. % ethanol, greater than about 65 wt. % ethanol, or greater than about 70 wt. % ethanol. In some embodiments, the liquid distillate composition can comprise greater than about 15 wt. % water, greater than about 20 wt. % water, or greater than about 25 wt. % water. In some embodiments, the liquid distillate composition can comprise less than about 20 wt. % C3-C6 alcohol, less than about 15 wt. % C3-C6 alcohol, or less than about 10 wt. % C3-C6 alcohol. In some embodiments, a portion of the liquid distillate can be used upstream of the recovery system. For example, all or some fraction of the liquid distillate can be used in a fermentation process for production of a C3-C6 alcohol (e.g., returned to a fermentor). In other embodiments, the liquid distillate can be refined to recover ethanol from the liquid distillate using processes known in the art (e.g., distillation, liquid-liquid extraction, etc.).

As noted above, a liquid distillate comprising water and ethanol produced by a rectification column is not reintroduced to the recovery system. By taking a liquid distillate out of the recovery system, significant advantages are achieved. A consequence of the presence of excess ethanol in the recovery system is that a dehydration column, discussed in further detail herein, cannot sufficiently purify or reduce the moisture content of the C3-C6 alcohol. An advantage provided by a dehydration column is that the dehydration column can dehydrate an alcohol-rich liquid phase to produce a dehydrated C3-C6 alcohol (e.g., comprising less than about 10 wt. % water, comprising less than about 9 wt. % water, comprising less than about 8 wt. % water, comprising less than about 7 wt. % water, comprising less than about 6 wt. % water, comprising less than about 5 wt. % water, comprising less than about 4 wt. % water, comprising less than about 3 wt. % water, comprising less than about 2 wt. % water, comprising less than about 1 wt. % water, comprising less than about 0.5 wt. % water, comprising less than about 0.1 wt. % water). Without removal of the ethanol in the liquid distillate from the rectification column, it will remain entrained in liquid distillate with a C3-C6 alcohol, and consequently preventing the dehydration column from producing an appropriately dehydrated C3-C6 alcohol product. For example, when producing a product to meet stringent maximum water requirements of a fuel grade specification, excess ethanol in a liquid distillate may result in a product having unacceptable high water content, which can require additional purification steps, such as water removal using molecular sieves.

A rectification column bottoms liquid can also be produced in the rectification column. The rectification bottoms can be recycled and combined with a feed stream in the recovery system. In some embodiments, the rectification bottoms liquid composition can comprise greater than about 45 wt. % water, greater than 50 wt. % water, or greater than about 54 wt. % water. In some embodiments, the rectification bottoms liquid composition can comprise less than about 1 wt. % ethanol, less than about 2 wt. % ethanol, less than about 3 wt. % ethanol or less than about 3.5 wt. % ethanol. In some embodiments, the rectification bottoms liquid can comprise greater than about 35 wt. % isobutanol, greater than about 40 wt. % isobutanol, or greater than about 45 wt. % isobutanol.

A rectification distillate vapor stream can also be produced in the rectification column. The rectification distillate vapor stream can be processed through a system in order to sub-cool and condense certain components of the rectification distillate vapor stream. These components can include a C3-C6 alcohol, water and ethanol, which can be recycled in the recovery system. Components that are not sub-cooled and condensed and that remain as a vapor (e.g., non-condensable gases such as such as carbon dioxide, nitrogen, oxygen, sulfur dioxide, carbon monoxide, etc.) can be vented from the system. In some embodiments, the rectification vapor stream composition can comprise greater than about 45 wt. % carbon dioxide, greater than about 50 wt. % carbon dioxide, or greater than about 55 wt. % carbon dioxide. In some embodiments, the rectification vapor stream composition can comprise greater than about 2 wt. % water, or greater than about 5 wt. % water. In some embodiments, the rectification vapor stream composition can comprise greater than about 20 wt. % ethanol, greater than about 25 wt. % ethanol or greater than about 30 wt. % ethanol.

As used herein, the rectification column can be any suitable device. In some embodiments, the rectification column contains trays. In other embodiments, the rectification column is a packed column.

In some embodiments, the only stream entering the rectification column can be a vapor stream from a stripping column and not other sources of water, C3-C6 alcohol or ethanol. For example, in one embodiment, the rectification column does not have more than the single incoming stream, for example, it does not have an overhead stream from a C3-C6 alcohol dehydration column or other recycle streams as an incoming stream.

Certain embodiments further include recovering a C3-C6 alcohol from the alcohol-rich liquid phase. In some embodiments, reference to recovering a C3-C6 alcohol refers to recovery of one alcohol, such as isobutanol. In other embodiments, recovering a C3-C6 alcohol refers to recovery of two or more C3-C6 alcohols as described herein. In one embodiment, the step of recovering can include conducting the C3-C6 alcohol-rich liquid phase to a dehydration column to dehydrate the C3-C6 alcohol and produce a dehydrated C3-C6 alcohol. In some embodiments, the dehydrated C3-C6 alcohol composition can comprise greater than about 94 wt. % C3-C6 alcohol, greater than about 95 wt. % C3-C6 alcohol, greater than about 96 wt. % C3-C6 alcohol or greater than about 97 wt. % C3-C6 alcohol. In some embodiments, the dehydrated C3-C6 alcohol can comprise less than about 1 wt. % water, less than about 0.5 wt. % water, less than about 0.25 wt. % water, or less than about 0.1 wt. % water. In some embodiments, the dehydrated C3-C6 alcohol can be further processed by conducting the dehydrated alcohol to a purification column (e.g., a distillation column) to purify the dehydrated C3-C6 alcohol to a solvent grade C3-C6 alcohol (e.g., comprising less than about 1.0 wt % water, less than about 0.9 wt % water, less than about 0.8 wt % water, less than about 0.7 wt % water, less than about 0.6 wt % water, less than about 0.5 wt % water, less than about 0.4 wt % water, less than about 0.3 wt % water, less than about 0.2 wt % water, less than about 0.1 wt % water, less than about 0.05 wt % water). The solvent grade C3-C6 alcohol can comprise greater than about 99.5 wt. % C3-C6 alcohol.

A vapor distillate can be produced in the dehydration column. The vapor distillate composition can comprise greater than about 25 wt. % water, greater than about 30 wt. % water, or greater than about 35 wt. % water. The vapor distillate composition can comprise greater than about 45 wt. % isobutanol, greater than about 50 wt. % isobutanol, greater than about 55 wt. % isobutanol, greater than about 60 wt. % isobutanol or greater than about 65 wt. % isobutanol.

As used herein, the dehydration column can be any suitable distillation column. In some embodiments, the dehydration column can be a trayed distillation column. In some embodiments, the dehydration column can be a packed distillation column.

As used herein, the term C3-C6 alcohols refers to an alcohol containing three, four, five, or six carbon atoms, including all of the isomers thereof, and mixtures thereof. In some embodiments, a single C3-C6 alcohol is produced. In one embodiment, the term C3-C6 alcohol can refer to a single C3, C4, C5, or C6 alcohol or a single isomer thereof. Thus, the C3-C6 alcohol can be selected from propanols, butanols, pentanols, and hexanols. More particularly, the C3 alcohol can be 1-propanol, or 2-propanol; the C4 alcohol can be 1-butanol, 2-butanol, tert-butanol (2-methyl-2-propanol), or isobutanol (2-methyl-1-propanol); the C5 alcohol can be 1-pentanol, 2-pentanol, 3-pentanol, 2-methyl-1-butanol, 3-methyl-1-butanol, 2-methyl-2-butanol, 3-methyl-2-butanol, or 2,2-dimethyl-1-propanol; and the C6 alcohol can be 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 3,3-dimethyl-1-butanol, 2,2-dimethyl-1-butanol, 2,3-dimethyl-1-butanol, 2,3-dimethyl-2-butanol, 3,3-dimethyl-2-butanol, or 2 ethyl-1-butanol. In one embodiment, the C3-C6 alcohol is isobutanol (2-methyl-1-propanol).

In various embodiments of the present invention, the C3-C6 alcohol is a renewable alcohol, that is, an alcohol that is produced, at least in part, using renewable resources. For example, the alcohol can be produced from biological materials or by biological processes, such as by culturing of microorganisms or fermentation. In such processes, the microorganisms metabolize substrates that are, or can be derived from, renewable materials to produce the C3-C6 alcohol. Renewable materials can include corn, sugar cane, and cellulosic materials, and are typically processed (e.g., chemically, enzymatically or thermally treated) so that various sugars are available for microorganisms.

Various streams can include impurities. The term "impurity" or "impurities" means any compound other than the alcohol or alcohols being purified. The term impurity can include any byproduct or co-product of the recovery process. Byproducts or co-products can include, among other compounds, water, acetaldehyde, acetic acid, ethanol, lactic acid, 1-propanol, glycerol, isobutylaldehyde, isobutyric acid, 1-butanol, 2,3-butanediol, 2-methyl-1-butanol, 3-methyl-1-butanol, isobutyl acetate, and 2-phenylethanol. In embodiments where the alcohol is a renewable alcohol, the impurities can be unique to renewable alcohols, as compared to conventionally produced alcohols. For example, renewable alcohol-containing compositions that are produced from cellulosic starting materials can include furfural, a heterocyclic aldehyde derived from cellulosic materials.

Some further embodiments of the present invention can include further distilling or flashing the rectification bottom liquid from a rectification column to remove ethanol from the rectification bottom liquid. In some embodiments, the processed bottom liquid composition can comprise water, ethanol and isobutanol. In some embodiments, the processed bottoms liquid can be conducted to a liquid-liquid separator or combined with a feed stream prior to introduction of the feed stream to a liquid-liquid separator.

Some embodiments further include processing the vapor distillate by sub-cooling the distillate to condense one or condensable components therein, which can then be recycled to the recovery system, and purge the non-condensable gases from the recovery system.

In another embodiment, the method to recover the C3-C6 alcohol from a feed stream is conducted in a retrofit ethanol production plant. The retrofitted ethanol production plant can include a stripping column and a rectification column. The stripping column used to produce a vapor stream comprising a C3-C6 alcohol, water and ethanol can be a beer column from the ethanol recovery system. An ethanol production plant generally contains a beer (stripping) column that removes solids and bulk water from the ethanol. The ethanol production plant also generally contains a second column or columns (e.g., rectification column(s)) that enrich(es) the ethanol to a near azeotropic mixture with water and a pure water stream. In some ethanol retrofit plants, there is only one distillation column that both removes solids and bulk water from ethanol and enriches ethanol to a near azeotropic mixture with water. When an ethanol production plant is retrofitted, the rectification column of the ethanol production plant can be used as the dehydration column in methods of the present invention for recovery of C3-C6 alcohol, and the stripping column of the ethanol production plant can be used as the stripping column in methods of the present invention for recovery of C3-C6 alcohol. In an alternative embodiment, the stripping column of the ethanol production plant can be retrofitted by partitioning the stripping column into two sections. One section of the partitioned stripping column strips water, ethanol and C3-C6 alcohol from a water-rich liquid phase (i.e., "section 1"). The second section of the partitioned rectification column dehydrates the C3-C6 alcohol from the C3-C6 alcohol-rich liquid phase (i.e., "section 2"). In further embodiments, the vapor produced in section 1 is fed into one of three stages at the bottom of section 2. The rectification column used to produce a liquid distillate comprising water and ethanol can be a partitioned ethanol stripping column. Typically, ethanol recovery systems employ the use of molecular sieves to dehydrate ethanol. However, the use of molecular sieves to dehydrate C3-C6 alcohols can result in significant recycle of product C3-C6 alcohols and increased operating costs for energy, maintenance and sieve beads, and increased sizing of the C3-C6 dehydration and the water purification columns. Accordingly, it is desirable to amply a method for dehydrating a C3-C6 alcohol which does not employ molecular sieves. Thus, in another embodiment, the present methods to recover a C3-C6 alcohol in a retrofit ethanol plant do not require the use of molecular sieves. Though molecular sieves can be present in the plant, the method to recover the C3-C6 alcohol in a retrofit ethanol plant can exclude the use of molecular sieves in dehydration of a C3-C3 alcohol.

In an alternative embodiment, the present invention includes a method to recover a C3-C6 alcohol from a feed stream in a recovery system. The feed stream comprises a C3-C6 alcohol and water. The method includes separating a water-rich liquid phase from an alcohol-rich liquid phase. The alcohol-rich liquid phase is conducted to a dehydration column to produce a bottoms fraction that includes greater than about 96 wt. % C3-C6 alcohol. In this step, lower boiling components in the alcohol-rich liquid phase are distilled and removed from the overhead of the dehydration column as a vapor stream, and the bottoms fraction comprises at least about 95 wt % C3-C6 alcohol, at least about 95 wt % C3-C6 alcohol, at least about 96 wt % C3-C6 alcohol, at least about 97 wt % C3-C6 alcohol, at least about 98 wt % C3-C6 alcohol.

In some embodiments, a vapor distillate can also be produced in the dehydration column. In some embodiments, the vapor distillate composition can comprise greater than about 25 wt. % water, greater than about 30 wt. % water, or greater than about 35 wt. % water. The vapor distillate composition can comprise greater than about 45 wt. % C3-C6 alcohol, greater than about 50 wt. % C3-C6, greater than about 55 wt. % C3-C6, greater than about 60 wt. % C3-C6 or greater than about 65 wt. % C3-C6. In some embodiments, the vapor distillate can be further conducted from the dehydration column and processed (e.g., distilled) to produce a liquid stream that can comprise a C3-C6 alcohol and a vapor stream that can comprise C3-C6 alcohol and water. The vapor stream can be further processed to sub-cool (e.g., condense) certain components of the vapor stream which can be recycled to the recovery system. Noncondensable components in the vapor stream can be vented from the system.

In some further embodiments, the liquid comprising C3-C6 alcohol can be conducted to a purification column to produce a purified liquid distillate. The purified liquid distillate composition can comprise greater than about 95 wt. % C3-C6 alcohol, greater than about 96 wt. % C3-C6 alcohol, greater than about 97 wt. % C3-C6 alcohol, greater than about 98 wt. % C3-C6 alcohol, greater than about 99 wt. % C3-C6 alcohol, greater than about 99.1 wt. % C3-C6 alcohol, greater than about 99.2 wt. % C3-C6 alcohol, greater than about 99.3 wt. % C3-C6 alcohol, greater than about 99.4 wt. % C3-C6 alcohol, greater than about 99.5 wt. % C3-C6 alcohol, greater than about 99.6 wt. % C3-C6 alcohol, or greater than about 99.7 wt. % C3-C6 alcohol. In some embodiments, the C3-C6 alcohol is a single species of alcohol (e.g., isobutanol).

Some embodiments further include conducting the bottoms fraction produced by conducting the alcohol-rich liquid phase from the dehydration column to a purification column to produce a purified liquid distillate. The purified liquid distillate composition can include greater than about 95 wt. % C3-C6 alcohol, greater than about 96 wt. % C3-C6 alcohol, greater than about 97 wt. % C3-C6 alcohol, greater than about 98 wt. % C3-C6 alcohol, greater than about 99 wt. % C3-C6 alcohol, greater than about 99.1 wt. % C3-C6 alcohol, greater than about 99.2 wt. % C3-C6 alcohol, greater than about 99.3 wt. % C3-C6 alcohol, greater than about 99.4 wt. % C3-C6 alcohol, greater than about 99.5 wt. % C3-C6 alcohol, greater than about 99.6 wt. % C3-C6 alcohol, or greater than about 99.7 wt. % C3-C6 alcohol. In another embodiment, the present invention provides an alcohol-containing composition. The composition can include at least about 94 wt. %, 95 wt. %, 96 wt. %, 97 wt. %, or 98 wt. %, butanol (e.g., isobutanol) and at least about 1.5 wt. %, 1.75 wt. %, 2 wt. %, 2.25 wt. %, or 2.5 wt. %, pentanol. In this embodiment, the pentanol can be any configuration of pentanol, but in some embodiments, is 2-methyl-1-butanol and/or 3-methyl-1-butanol. The alcohol-containing composition can also have less than about 2 wt. %, 1.5 wt. %, 1.25 wt. %, 1 wt. %, or 0.75 wt. % water. In an alternative embodiment, the composition can comprise at least about 99.1 wt. %, 99.2 wt. %, 99.3 wt. %, 99.4 wt. %, or 99.5 wt. % butanol (e.g., isobutanol) and a C3-C6 alcohol, other than butanol, in an amount less than about 1 wt. %, 0.9 wt. %, 0.8 wt. %, 0.7 wt. %, 0.6 wt. % or 0.5 wt. %. In some embodiments, the butanol can be a renewable butanol. Accordingly, in some embodiments, the alcohol-containing composition can include impurities or contaminants that are characteristic of biological materials or biological processes. In some embodiments, the alcohol-containing composition can be produced using a method to recover a C3-C6 alcohol from a feed stream as described herein.

One alcohol-containing composition of the present invention comprises least about 94 wt. %, 95 wt. %, 96 wt. %, 97 wt. %, or 98 wt. %, isobutanol. The composition can have less than about 2 wt. %, 1.5 wt. %, 1.25 wt. %, 1 wt. %, or 0.75 wt. % water. In some embodiments, the alcohol-containing composition can also comprise impurities, but comprises a low enough concentration of impurities so that a desired minimum content of isobutanol, e.g., as referenced herein, is met. For example, the total impurities, such as one or more of acetaldehyde, acetic acid, ethanol, lactic acid, 1-propanol, glycerol, isobutylaldehyde, isobutyric acid, 1-butanol, 2,3-butanediol, 2-methyl-1-butanol, 3-methyl-1-butanol, isobutyl acetate, and 2-phenylethanol, can be present in the composition in amounts less than about 6 wt. %, 5 wt. %, 4 wt. %, 3 wt. %, 2 wt. % or 1 wt. %. In a specific embodiment, an alcohol-containing composition comprises acetic acid, ethanol, lactic acid, 1-propanol, isobutyric acid, 1-butanol, 2,3-butanediol, 2-methyl-1-butanol, 3-methyl-1-butanol, isobutyl acetate, and 2-phenylethanol in amounts less than about 6 wt. %, 5 wt. %, 4 wt. %, 3 wt. %, 2 wt. % or 1 wt. %. This composition can be a renewable isobutanol composition.

Another alcohol-containing composition of the present invention comprises least about 99.2 wt. %, 99.3 wt. %, 99.4 wt. %, 99.5 wt. %, or 99.6 wt. %, isobutanol. The composition can have less than about 0.25 wt. %, 0.2 wt. %, 0.15 wt. %, 0.1 wt. %, or 0.05 wt. % water. In some embodiments, the alcohol-containing composition can also comprise impurities, but may contain a low enough concentration of impurities so that the minimum content of isobutanol as referenced above is met. For example, the total impurities, such as one or more of acetaldehyde, acetic acid, ethanol, lactic acid, 1-propanol, glycerol, isobutylaldehyde, isobutyric acid, 1-butanol, 2,3-butanediol, 2-methyl-1-butanol, 3-methyl-1-butanol, isobutyl acetate, and 2-phenylethanol, can be present in the composition in amounts less than about 0.8 wt. %, 0.7 wt. %, 0.6 wt. %, 0.5 wt. %, 0.4 wt. % or 0.3 wt. %. In a specific embodiment, a composition comprises ethanol, 1-5 propanol, 1-butanol, 2-methyl-1-butanol, 3-methyl-1-butanol, and isobutyl acetate in amounts less than about 0.8 wt. %, 0.7 wt. %, 0.6 wt. %, 0.5 wt. %, 0.4 wt. % or 0.3 wt. %. This composition can be a renewable isobutanol composition.

The alcohol-containing compositions disclosed herein can additionally meet various regulatory and/or voluntary standards or specifications for classes of products. Such alcohol-containing compositions can be useful for a variety of applications, such as fuel compositions or for use as solvents in conventional applications. For example, the federal government and state governments in the United States regulate automobile fuels and related emissions from the combustion thereof. In addition, non-governmental organizations, such as ASTM International, develop voluntary standards for certain product categories.

Another embodiment of the present invention is a method to recover a C3-C6 alcohol from a stream comprising a C3-C6 alcohol and water in a recovery system. A water-rich liquid phase is separated from a C3-C6 alcohol-rich liquid phase. The water-rich liquid phase is conducted to a first stripping section of a column to remove a vapor stream comprising a C3-C6 alcohol, ethanol and water from the water-rich liquid phase. An alcohol-rich liquid phase is conducted to a second dehydration section of the column to remove water from the C3-C6 alcohol-rich liquid phase.

In some embodiments, the column can be a partitioned stripper column from an ethanol production plant. In another embodiment, an overhead vapor stream from the first stripper section is fed to a rectification column to remove water and ethanol from the vapor stream.

Another embodiment of the present invention includes a method to retrofit an ethanol production plant, wherein a stripper column is partitioned to provide a dual function column. The dual function column comprises an inlet for a water-rich liquid phase comprising C3-C6 alcohol, ethanol and water. The column comprises a first stripper section to remove a vapor stream comprising C3-C6 alcohol, ethanol and water from the water-rich liquid phase. The column further comprises an inlet for a C3-C6 alcohol-rich liquid phase. The column also comprises a second dehydration section to remove water from the C3-C6 alcohol-rich liquid phase.

Another embodiment of the present invention is a dual function column for recovery of a C3-C6 alcohol. The column has an inlet for a water-rich liquid phase, a first stripper section of the column to remove a vapor stream comprising C3-C6 alcohol, water and ethanol from the water-rich liquid phase; an inlet for a C3-C6 alcohol-rich liquid phase and a second dehydration section of the column to remove water from the C3-C6 alcohol-rich liquid phase.

Figure 1:
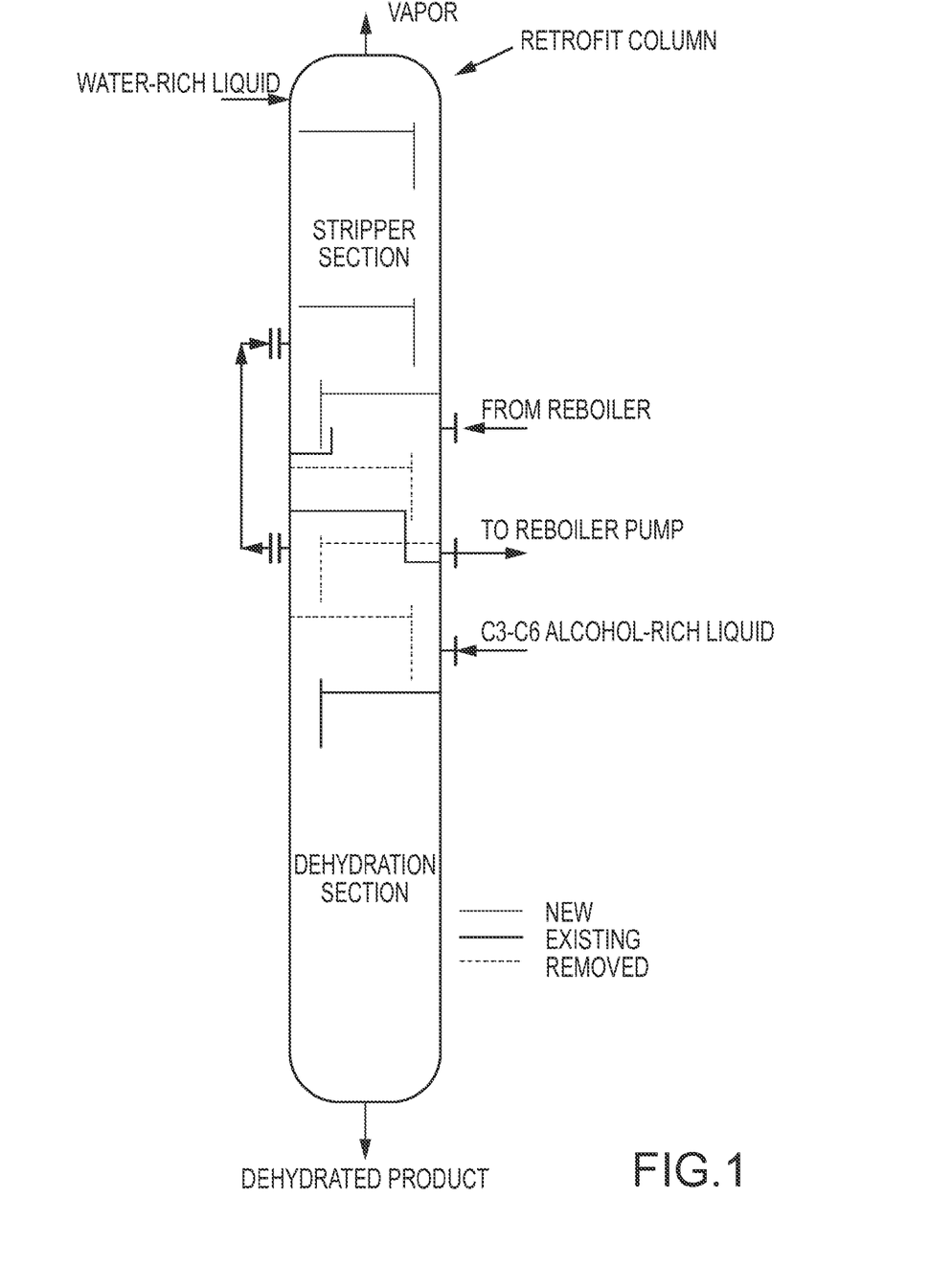
FIG. 1 illustrates a partitioned retrofitted stripping column.

FIG. 1 illustrates a partitioned retrofitted column. The retrofit column can be an existing column in an ethanol production plant. The top portion of the retrofitted column can be used as a stripping column, while the bottom portion of the column can be used as a dehydration column. Retrofitting the column can reduce operating and equipment costs for the recovery plant. Water-rich liquid can be fed into the top of the retrofit column. The stripper section of the column can be equipped with trays. Additional trays can be added as necessary. Alternatively, trays can also be removed as necessary. Liquid bottoms exit the stripper section and can be processed in a reboiler. The vapor produced in the stripper section can be further processed to remove water and ethanol from the vapor stream. The C3-C6 alcohol-rich liquid is fed to the top of the dehydration column. A dehydrated C3-C6 alcohol-rich liquid is produced in the dehydration column. Vapors from the dehydration column can be recycled to the stripper section.

Figure 2:
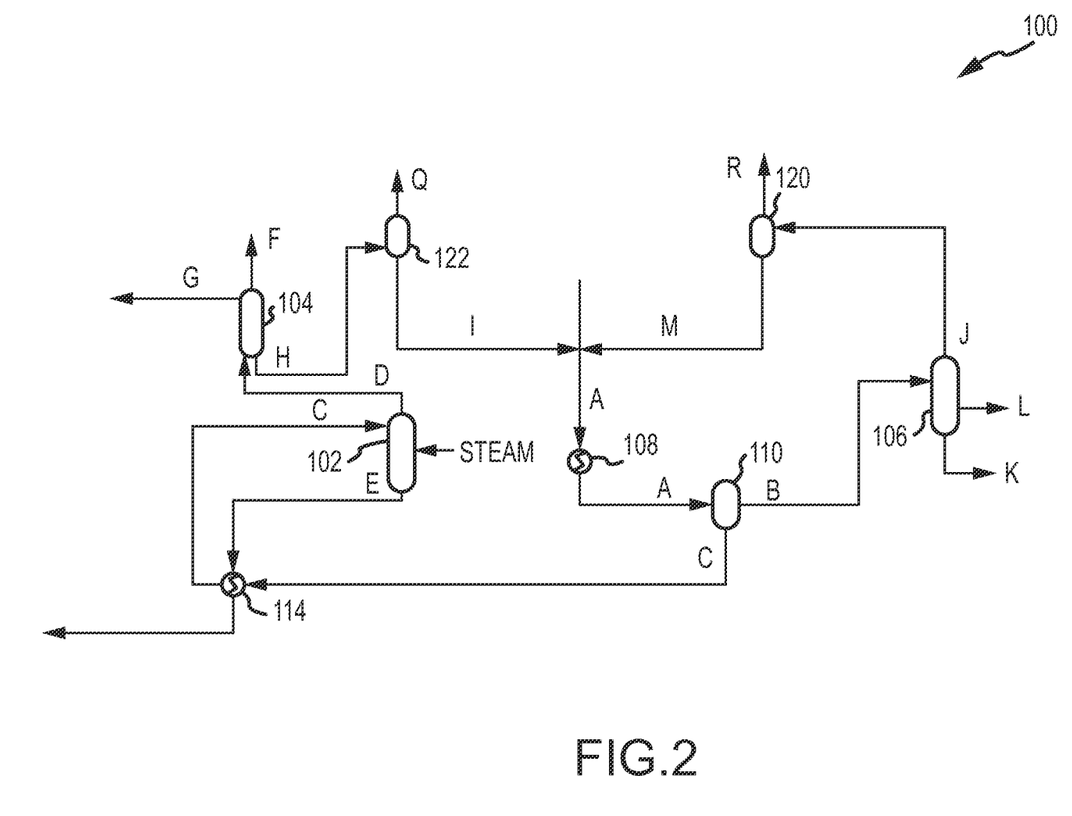
FIG. 2 illustrates a recovery system for recovering a C3-C6 alcohol from a feed stream.

An embodiment of the present invention is illustrated in FIG. 2. FIG. 2 illustrates a recovery system 100. The recovery system 100 can include several columns, such as a stripper column 102, a dehydration column 106, and a rectification column 104. The recovery system 100 also includes at least one liquid-liquid separator 110.

In operation, a feed stream (A) is fed through an optional heat exchanger 108. The feed stream (A) will have a composition so that two phase liquids that are immiscible can be formed from the feed stream (A) or from the mixture of streams after the start of one or more of the columns. In some embodiments, the feed stream (A) can comprise at least a portion of a fermentation broth. For example, as described in U.S. Pat. No. 8,101,808, C3-C6 alcohols can be recovered from a fermentation broth to produce a C3-C6 alcohol-rich phase and a water-rich phase, and these can be fed into the recovery system of the present invention. In other words, feed streams of the present invention can be derived from a portion of the fermentation broth, i.e., can comprise at least a portion of a fermentation broth. After the feed stream (A) exits the optional heat exchanger 108, the feed stream (A) is sent to a liquid-liquid separator 110. It is understood that multiple liquid-liquid separators can be used. The liquid-liquid separator 110 separates the two liquid phases formed from the feed stream. One liquid phase produced in the liquid-liquid separator 110 is a C3-C6 alcohol-rich liquid stream (B). The C3-C6 alcohol-rich liquid stream (B) is sent to a dehydration column 106. The second stream produced in the liquid-liquid separator 110 is a water-rich liquid (C).

The water-rich liquid (C) can pass through an optional pump and then through an optional heat exchanger 114, which can increase the temperature of the water-rich liquid (C) to between about 60° F. and about 105° F., preferably about 98.5° F. Optional pumps can be used throughout the recovery system 100 to direct the flow of various fluids. Optional heat exchangers can also be used throughout the recovery system 100 in order to regulate the temperature of various fluids. The water-rich liquid stream (C) can include water, ethanol and C3-C6 alcohol. In some embodiments, the water-rich liquid (C) can be greater than about 90 wt. % water and less than about 4 wt. % C3-C6 alcohol. The water-rich liquid (C) is conducted to the stripper column 102. In this embodiment, only a single stream (C) containing recoverable materials is introduced into the stripper column 102, which has the advantage of stream (C) not being diluted by being mixed with a more dilute stream. It will be noted that stream (C) can be introduced into the stripper column 102 at multiple points. Steam can also supplied to the system. In one embodiment, the stripper column 102 can be a six theoretical stage distillation column. In some embodiments, the pressure at the top of the column can be about 6 psia and the pressure differential across the stripper column 102 can be about 1.5 psi. In some embodiments, the heat transfer can be about 19 MMBtu/hour. The stripper column 102 can produce a vapor stream (D) and a liquid stream (E). The composition of the liquid stream (E) can be predominately water. The liquid stream (E) can provide a heating source to a heat exchanger, for example the optional heat exchanger 114, before it is recycled out of the recovery system 100.

The vapor stream (D) from the stripper column 102 is conducted to the rectification column 104. In this embodiment, only a single stream (D) containing recoverable materials is introduced into the rectification column 104, which has the advantage of stream (D) not being diluted by being mixed with a more dilute stream. It will be noted that stream (D) can be introduced into the rectification column 104 at multiple points. The rectification column 104 can be a six theoretical stage column and can contain a partial condenser. The pressure at the top of the rectification column 104 can be around 5 psia and the pressure differential across the rectification column 104 can be about 1.0 psi. In some embodiments, the heat transfer can be about 3.4K Btu/gal isobutanol product (~20 MMBtu/hour). The rectification column 104 can produce a vapor distillate (F), a liquid distillate (G), and a rectification bottoms liquid stream (H). The rectification bottom liquid stream (H) can be directed to a flash dryer 122, wherein the liquids (I) exiting the flash dryer can be recycled to the feed stream (A). The liquid distillate (G) composition can comprise greater than about 50 wt. % ethanol. The liquid distillate (G) can be removed from the recovery system 100 where it can be used in other operations upstream of the recovery system 100 or further processed for other applications. The liquid distillate (G) can be advantageously removed from the recovery system 100 thereby removing a stream comprising a majority of ethanol.

In some embodiments, the recovery system 100 can be a retrofit ethanol production plant. The stripper 102 can be the column commonly referred to as the stripper or side-stripper from the retrofit ethanol process. In another embodiment, the rectification column can be a partitioned section of the column commonly referred to as the stripper or side-stripper column from the retrofit ethanol process.

The C3-C6 alcohol-rich liquid (B) exiting the liquid-liquid separator 110 is directed to the dehydration column 106. An optional pump can be used to pump the C3-C6 alcohol-rich liquid (B) to the dehydration column 106. The C3-C6 alcohol-rich liquid (B) is directed to the dehydration column 106. In some embodiments, the dehydration column 106 can be a column containing 18 stages and a reboiler. In some embodiments, the pressure at the top of the dehydration column 106 can be about 7 psia and the pressure differential across the dehydration column 106 can be about 2 psi. In some embodiments, the heat transfer can be about 4.3K Btu/gal isobutanol product (23 MMBtu/hour). The C3-C6 alcohol-rich liquid (B) entering the dehydration column can comprise isobutanol and water. In some embodiments, the concentration of the isobutanol in the C3-C6 alcohol-rich liquid (B) is greater than about 60 wt. %. The dehydration column produces a vapor distillate (J) and a bottoms liquid stream (K). The vapor distillate (J) can comprise isobutanol and water. In some embodiments, the vapor distillate (J) components can include at least about 50 wt. % isobutanol. In some embodiments, the vapor distillate (J) can be condensed and returned to the liquid-liquid separator (stream M). In some embodiments, the dehydration column 106 can include a side draw to remove a side draw stream (L) that can be useful in a fuel product, such as a fuel grade isobutanol for example, the 96 wt. % isobutanol compositions described herein. In some embodiments, the side draw stream (L) can sufficiently meet the specifications of a fuel grade alcohol. In other embodiments, the side draw stream (L) can be recycled to the feed stream. The bottoms liquid stream (K) exiting the dehydration column can comprise at least about 97 wt. % isobutanol.

Figure 3:
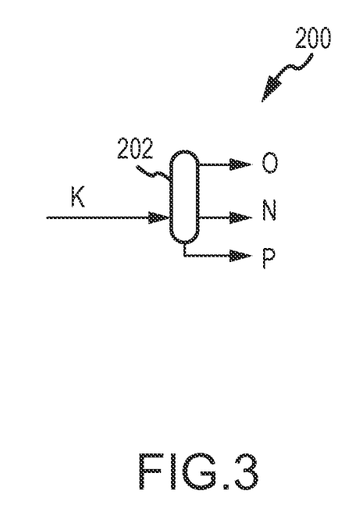
FIG. 3 illustrates a purification process for purifying a C3-C6 alcohol.

If a sufficient amount of water is not removed in the dehydration column (FIG. 2-106), then a product side draw (N) can be used in purification column (FIG. 3-202). In another embodiment, a sufficient amount of water is removed in the dehydration column, and a product side draw can be used in purification column to remove an impurity (e.g., as described herein) from the alcohol.

Alternatively, the dehydration column 106 can include a side draw to remove a side draw stream (L) that can be suitable useful as a fuel product, including a sufficiently low acid content. If the acid is isobutyric acid, then the bottoms stream (K) would be discarded.

In still other embodiments, the side stream (L) can be used to remove a C3-C6 alcohol product that can be used as a fuel, while the bottoms stream (K) is further processed to produce a solvent C3-C6 alcohol product.

Another aspect of the invention is illustrated in FIG. 3. FIG. 3 illustrates a purification system for purifying an isobutanol (bottoms product of dehydration column 106) that can be used as a fuel to an isobutanol that can be used as a solvent.

The purification system 200 can comprise a purification column 202. Optional pumps can be used throughout the purification system 200 to direct the flow of various fluids. Optional heat exchangers can also be used throughout the purification system 200 in order to regulate the temperature of various fluids. The isobutanol (K) is fed to the purification column 202. In some embodiments, the purification column 202 can include thirty stages, a total condenser and a reboiler. In some embodiments, the pressure at the top of the purification column 202 can be about 2 psig and the pressure differential across the purification column 202 can be about 4 psi. In some embodiments, the heat transfer of the condenser can be about 2.8K Btu/gal isobutanol product (−14 MMBtu/hour), while the heat transfer of the reboiler can be about 3.7K Btu/gal isobutanol product (19 MMBtu/hour). A liquid distillate (O) and distillate bottoms (P) are produced in the purification column 202. In some embodiments if a sufficient amount of water is not removed in the dehydration column (FIG. 2-106), then a product side draw (N) can also be removed from the purification column 202. In another embodiment, a sufficient amount of water is removed in the dehydration column, and a product side draw can be used in the purification column to remove an impurity (e.g., as described herein) from the alcohol. The composition of the liquid distillate (O) exiting the purification column 202 can include greater than about 99 wt. % isobutanol. In some embodiments, the composition of isobutanol in the liquid distillate (O) can be greater than about 99.6 wt. %. The composition of the distillate bottoms (P) produced in the purification column 202 can include 3-methyl-1-butanol. In some embodiments, the composition of the distillate bottoms (P) can include greater than about 44.2 wt. % 3-methyl-1-butanol.

As used herein, "comprises" and "comprising" include within their scope all narrower terms, such as "consisting essentially of" and "consisting of" as alternative embodiments of the present invention characterized herein by "comprises" or "comprising". In regard to use of "consisting essentially of", this phrase limits the scope of a claim to the specified steps and materials and those that do not materially affect the basic and novel characteristics of the invention disclosed herein. The basic and novel characteristics of the invention can be the purification of compositions comprising C3-C6 alcohols or compositions produced thereby or a combination of the foregoing.

EXAMPLES

For purposes of illustration, reference is made to the systems described in FIGS. 2 and 3 in Examples 1 and 2 below, though it is to be understood that the systems of FIGS. 2 and 3 are not limited by the specific Examples in this section.

Example 1

This example illustrates an embodiment of the present invention in which an alcohol dehydration column removes water to a level of less than or equal to 0.1 wt. % from an alcohol-rich liquid phase.

In this simulation, the recovery system 100 includes a liquid-liquid separator 110 that produces a water-rich liquid phase (C) and an isobutanol-rich liquid phase (B). The system also includes a stripper column 102 and a rectification column 104 that process the water-rich liquid phase (C), as well as a dehydration column 106 that processes the isobutanol-rich liquid phase (B).

The stripper column 102 has six theoretical stages and a reboiler. The rectification column 104 has six theoretical stages and a partial condenser, and produces two liquid phases and a bottoms product. The dehydration column 106 has eighteen stages and a reboiler.

The water-rich liquid phase (C) is sent to the stripper column 102 that produces a vapor stream (D) that includes water, ethanol and isobutanol, and a bottoms stream (E) that includes primarily water. The composition of the various feed and exiting streams of the stripper column is shown below in Table 1.

TABLE 1

| | Stream as illustrated in FIG. 2 | | | |
|---|---|---|---|---|
| | Stream C LIQUID | Steam VAPOR | Stream D VAPOR | Stream E LIQUID |
| Temperature F. | 161 | 201 | 161 | 179 |
| Pressure psia | 19.7 | 11.8 | 6.0 | 7.5 |
| Mass Flow lb/hr | 262,000 | 5,000 | 31,000 | 226,000 |
| | Composition wt. % | | | |
| Water | 93.92% | 99.79% | 52.70% | 99.68% |
| Acetic acid | 0.01% | 0.14% | 0.00% | 0.02% |
| Ethanol | 1.01% | 0.00% | 6.60% | 0.23% |
| 1-propanol | 0.02% | 0.00% | 0.14% | 0.00% |
| Isobutyric acid | 0.05% | 0.06% | 0.02% | 0.05% |
| Isobutanol | 4.94% | 0.01% | 40.23% | 0.02% |
| 2-methyl-1-butanol | 0.00% | 0.00% | 0.04% | 0.00% |
| 3-methyl-1-butanol | 0.03% | 0.00% | 0.28% | 0.00% |

The stage profiles in the stripper column are shown below in Table 2.

TABLE 2

| Theoretical Stage | Temp F. | Pressure psia | Heat Duty MMBtu/hr | Liquid lb/hr | Vapor lb/hr |
|---|---|---|---|---|---|
| 1 | 161.2 | 6.0 | 0 | 249,000.0 | 31,000.0 |
| 2 | 165.3 | 6.3 | 0 | 248,000.0 | 28,000.0 |
| 3 | 169.0 | 6.5 | 0 | 246,000.0 | 26,000.0 |
| 4 | 172.2 | 6.8 | 0 | 246,000.0 | 25,000.0 |
| 5 | 174.9 | 7.0 | 0 | 246,000.0 | 24,000.0 |
| 6 | 177.3 | 7.3 | 0 | 245,000.0 | 24,000.0 |
| Reboiler | 179.4 | 7.5 | 18.8 | 226,000.0 | 24,000.0 |

The vapor distillate from the stripper column is sent to the rectification column that produces a vapor distillate, a liquid distillate and a bottoms fraction. The composition of the various feed and exiting streams of the stripper column is shown below in Table 3.

TABLE 3

| | Streams as illustrated in FIG. 2 | | | |
|---|---|---|---|---|
| | Stream I VAPOR | Stream Q VAPOR | Stream G LIQUID | Stream H 2-LIQ-PH |
| Temperature F. | 161 | 97 | 97 | 157 |
| Pressure psia | 6.0 | 5.0 | 5.0 | 6.0 |
| Mass Flow lb/hr | 31,100.0 | 200.0 | 1,500.0 | 29,400.0 |
| | Composition wt. % | | | |
| Water | 52.70% | 15.71% | 21.88% | 54.33% |
| Acetic acid | 0.00% | 0.00% | 0.00% | 0.00% |
| Ethanol | 6.60% | 80.69% | 66.41% | 3.42% |
| 1-propanol | 0.14% | 0.22% | 0.46% | 0.12% |
| Isobutyric acid | 0.02% | 0.00% | 0.00% | 0.02% |
| Isobutanol | 40.23% | 3.38% | 11.24% | 41.77% |
| 2-methyl-1-butanol | 0.04% | 0.00% | 0.00% | 0.04% |
| 3-methyl-1-butanol | 0.28% | 0.00% | 0.01% | 0.29% |

The stage profiles in the rectification column are shown below in Table 4.

TABLE 4

| Theoretical Stage | Temp F. | Pressure psia | Heat Duty MMBtu/hr | Liquid 1 b/hr | Vapor 1 b/hr | Theoretical Stage |
|---|---|---|---|---|---|---|
| Condenser | 97.0 | 5.0 | −19.9 | 37,600 | 0 | 200 |
| 2 | 137.1 | 5.2 | 0 | 0 | 36,300 | 37,900 |
| 3 | 144.3 | 5.3 | 0 | 0 | 35,600 | 38,100 |

TABLE 4-continued

| Theoretical Stage | Temp F. | Pressure psia | Heat Duty MMBtu/hr | Liquid l b/hr | Vapor l b/hr | Theoretical Stage |
|---|---|---|---|---|---|---|
| 4 | 149.1 | 5.5 | 0 | 32,300 | 3,100 | 37,300 |
| 5 | 152.4 | 5.7 | 0 | 28,000 | 7,100 | 37,200 |
| 6 | 154.8 | 5.8 | 0 | 26,500 | 8,400 | 36,800 |
| 7 | 156.6 | 6.0 | 0 | 16,000 | 13,300 | 36,600 |

The liquid distillate stream from the rectification column comprises about 21.4 wt. % water, 65.0 wt. % ethanol and about 11.0 wt. % isobutanol. This stream is taken out of the recovery system and no portion of it is reintroduced into the recovery system. The bottoms stream from the rectification column is reintroduced to the recovery system by being combined with the feed stream to the liquid-liquid separator.

The isobutanol-rich liquid phase is sent to the dehydration column that produces a vapor distillate, and a bottoms stream that includes primarily isobutanol. The composition of the various feed and exiting streams of the dehydration column is shown below in Table 5.

TABLE 5

| | Streams as illustrated in FIG. 2 | | |
|---|---|---|---|
| | Stream B LIQUID | Stream J VAPOR | Stream K LIQUID |
| Temperature F. | 107 | 162 | 203 |
| Pressure psia | 9.0 | 7.0 | 9.0 |
| Mass Flow lb/hr | 70,000.0 | 36,000.0 | 34,000.0 |
| Composition wt % | | | |
| Water | 18.00% | 34.94% | 0.10% |
| Acetic acid | 0.02% | 0.00% | 0.04% |
| Ethanol | 3.27% | 6.35% | 0.02% |
| 1-propanol | 0.13% | 0.15% | 0.10% |
| Isobutyric acid | 0.32% | 0.02% | 0.65% |
| Isobutanol | 77.18% | 58.15% | 97.29% |
| 2-methyl-1-butanol | 0.11% | 0.04% | 0.18% |
| 3-methyl-1-butanol | 0.96% | 0.35% | 1.61% |

The stage profiles in the stripper column are shown below in Table 6.

TABLE 6

| Theoretical Stage | Temp F. | Pressure psia | Heat Duty MMBtu/hr | Liquid lb/hr | Vapor lb/hr |
|---|---|---|---|---|---|
| 1 | 161.6 | 7.0 | 0 | 75,600 | 35,800 |
| 2 | 162.4 | 7.1 | 0 | 75,600 | 42,000 |
| 4 | 163.8 | 7.3 | 0 | 75,600 | 42,000 |
| 6 | 165.1 | 7.6 | 0 | 75,600 | 42,000 |
| 8 | 166.3 | 7.8 | 0 | 75,700 | 42,100 |
| 10 | 167.6 | 8.0 | 0 | 75,900 | 42,200 |
| 12 | 168.9 | 8.2 | 0 | 76,900 | 42,500 |
| 14 | 172.5 | 8.4 | 0 | 87,000 | 46,000 |
| 16 | 188.7 | 8.7 | 0 | 112,000 | 65,900 |
| 18 | 200.6 | 8.9 | 0 | 123,700 | 86,400 |
| Reboiler | 202.9 | 9.0 | 22.9 | 33,600 | 90,100 |

The bottoms stream from the dehydration column is the recovery stream and comprises about 97.3 wt. % isobutanol and about 0.1 wt. % water. This stream also includes pentanol components, namely 2-methyl-1-butanol at about 0.18 wt. % and 3-methyl-1-butanol at about 1.6 wt. %.

This example demonstrates that in methods of the present invention, isobutanol can be recovered in high yields with a low water content. This result can be achieved without the need or use of molecular sieves for drying the isobutanol.

Example 2

This example illustrates a composition of the present invention. Stream K from Example 1 is an isobutanol-containing composition of the present invention having the component percentages in Table 7.

TABLE 7

| Water | 0.10% |
|---|---|
| Acetic acid | 0.04% |
| Ethanol | 0.02% |
| 1-propanol | 0.10% |
| Isobutyric acid | 0.65% |
| Isobutanol | 97.29% |
| 2-methyl-1-butanol | 0.18% |
| 3-methyl-1-butanol | 1.61% |

Example 3

This example illustrates an embodiment of the present invention in which solvent grade isobutanol is produced.

In this simulation, the product stream from Example 1 is further processed. The product stream from Example can be useful as a possible fuel isobutanol product. This product stream is conducted to a purification column for further processing.

The purification column has thirty stages, a total condenser and a reboiler.

The isobutanol product is sent to the purification column that produces a liquid distillate stream that includes solvent grade isobutanol, and a bottoms stream that includes recoverable heavy ends. The composition of the various feed and exiting streams of the purification column is shown below in Table 8.

TABLE 8

| | Streams as illustrated in FIG. 3 | | |
|---|---|---|---|
| | Stream K LIQUID | Stream O LIQUID | Stream P LIQUID |
| Temperature F. | 117 | 232 | 274 |
| Pressure psia | 30.0 | 16.7 | 20.7 |
| Mass Flow lb/hr | 33,600 | 32,500 | 1,100 |
| Composition wt. % | | | |
| Water | 0.10% | 0.10% | 0.00% |
| Acetic acid | 0.04% | 0.00% | 1.30% |
| Ethanol | 0.02% | 0.02% | 0.00% |
| 1-propanol | 0.10% | 0.11% | 0.00% |
| Isobutyric acid | 0.65% | 0.00% | 19.71% |
| Isobutanol | 97.29% | 99.61% | 29.43% |
| 2-methyl-1-butanol | 0.18% | 0.03% | 4.66% |
| 3-methyl-1-butanol | 1.61% | 0.13% | 44.90% |

The stage profiles in the purification column are shown below in Table 9.

TABLE 9

| Theoretical Stage | Temp F. | Pressure psia | Heat Duty MMBtu/hr | Liquid lb/hr | Vapor lb/hr |
|---|---|---|---|---|---|
| Condenser | 231.59 | 16.70 | −13.9 | 58,000 | 0 |
| 2 | 235.08 | 17.70 | 0 | 35,000 | 58,000 |

TABLE 9-continued

| Theoretical Stage | Temp F. | Pressure psia | Heat Duty MMBtu/hr | Liquid lb/hr | Vapor lb/hr |
|---|---|---|---|---|---|
| 6 | 236.40 | 18.10 | 0 | 35,000 | 67,500 |
| 10 | 237.60 | 18.50 | 0 | 35,000 | 67,500 |
| 14 | 238.77 | 18.90 | 0 | 35,000 | 67,500 |
| 18 | 240.12 | 19.30 | 0 | 82,600 | 81,400 |
| 22 | 241.25 | 19.70 | 0 | 82,800 | 81,600 |
| 26 | 242.72 | 20.10 | 0 | 83,000 | 81,800 |
| 30 | 249.92 | 20.50 | 0 | 83,700 | 82,200 |
| 31 | 257.91 | 20.60 | 0 | 85,300 | 82,500 |
| Reboiler | 273.83 | 20.70 | 19.0 | 1,100 | 84,200 |

This example demonstrates that in methods of the present invention, solvent grade isobutanol products can be produced. The isobutanol composition in this example had 99.6 wt. % isobutanol and 0.1 wt. % water. The recovery of isobutanol as a solvent grade product was about 98%.

Example 4

This example illustrates a composition of the present invention. Stream O from Example 3 is an isobutanol-containing composition of the present invention having the component percentages in Table 10.

TABLE 10

| | |
|---|---|
| Water | 0.10% |
| Acetic acid | 0.00% |
| Ethanol | 0.02% |
| 1-propanol | 0.11% |
| Isobutyric acid | 0.00% |
| Isobutanol | 99.61% |
| 2-methyl-1-butanol | 0.03% |
| 3-methyl-1-butanol | 0.13% |

Example 5

Example 5 illustrates the purification of a C3-C6 alcohol-rich phase. In this example, the dehydration column 106 processes a C3-C6 alcohol-rich phase (B). The composition of the various feed and exiting streams of the dehydration column 106 is shown below in Table 11.

TABLE 11

| | Stream as illustrated in FIG. 2 | | | |
|---|---|---|---|---|
| | Stream B | Steam J | Stream L | Stream K |
| Temperature F. | 162 | 162 | 198 | 234 |
| Pressure psia. | 12 | 11 | 8.1 | 9 |
| Mass Flow lb/hr | 70,900 | 37,300 | 33,000 | 600 |
| | Composition wt. % | | | |
| Water | 18.12% | 34.06% | 0.50% | 0.00% |
| Acetic acid | 0.02% | 0.00% | 0.00% | 2.49% |
| Ethanol | 3.38% | 6.36% | 0.08% | 0.00% |
| 1-propanol | 0.13% | 0.15% | 0.10% | 0.00% |
| Isobutyric acid | 0.08% | 0.00% | 0.00% | 9.33% |
| Isobutanol | 77.21% | 59.03% | 98.65% | 19.18% |
| 2-methyl-1-butanol | 0.11% | 0.04% | 0.08% | 5.79% |
| 3-methyl-1-butanol | 0.95% | 0.36% | 0.57% | 63.20% |

Table 12 illustrates the theoretical stage profile for the dehydration column 106 and reboiler of Example 5.

TABLE 12

| Theoretical Stage | Temp F. | Pressure psm | Heat Duty MMBtu/hr | Liquid lb/hr | Vapor lb/hr |
|---|---|---|---|---|---|
| 1 | 161.9 | 7.0 | 0 | 70,700 | 37,300 |
| 2 | 162.7 | 7.1 | 0 | 70,700 | 37,100 |
| 4 | 164.1 | 7.3 | 0 | 71,200 | 37,200 |
| 6 | 167.0 | 7.6 | 0 | 77,000 | 39,100 |
| 8 | 180.2 | 7.8 | 0 | 97,400 | 52,400 |
| 10 | 195.0 | 8.0 | 0 | 111,200 | 72,800 |
| 12 | 199.1 | 8.2 | 0 | 113,800 | 112,600 |
| 14 | 201.2 | 8.4 | 0 | 114,300 | 113,500 |
| 16 | 205.8 | 8.7 | 0 | 115,100 | 114,000 |
| 18 | 220.9 | 8.9 | 0 | 119,500 | 115,800 |
| Reboiler | 234.4 | 9.0 | 28.5 | 600 | 118,900 |

Example 6

This example illustrates a composition of the present invention. Stream L from Example 5 is an isobutanol-containing composition of the present invention having the component percentages in Table 13.

TABLE 13

| | |
|---|---|
| Water | 0.50% |
| Acetic acid | 0.00% |
| Ethanol | 0.08% |
| 1-propanol | 0.10% |
| Isobutyric acid | 0.00% |
| Isobutanol | 98.65% |
| 2-methyl-1-butanol | 0.08% |
| 3-methyl-1-butanol | 0.57% |

Various aspects of the invention are described in detail in the examples provided below. However, these examples are provided for the purpose of illustration and are not intended to limit the scope of the present invention. Each publication and reference cited herein is incorporated herein by reference in its entirety. While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to recover a C3-C6 alcohol from a stream comprising C3-C6 alcohol, ethanol and water in a recovery system, comprising:
    a. separating a water-rich liquid phase from a C3-C6 alcohol-rich liquid phase;
    b. conducting the water-rich liquid phase to a column to produce a vapor stream comprising water and ethanol;
    c. conducting the vapor stream to a rectification column to produce a liquid distillate comprising water and ethanol, wherein the liquid distillate is not reintroduced to the recovery system; and
    d. recovering C3-C6 alcohol from the alcohol-rich liquid phase.

2. The method of claim 1, wherein the vapor stream is enriched in low molecular weight alcohols.

3. The method of claim 2, wherein the low molecular weight alcohols comprise C2 and C3 alcohols.

4. The method of claim 1, further comprising conducting the C3-C6 alcohol-rich liquid phase to a dehydration column to dehydrate the C3-C6 alcohol and produce a C3-C6 dehydrated alcohol comprising less than about 1 wt % water and greater than about 96 wt. % of a single C3-C6 alcohol.

5. The method of claim 4, further comprising conducting the greater than about 96 wt. % C3-C6 alcohol to a purification column to purify the C3-C6 alcohol to solvent grade C3-C6 alcohol.

6. The method of claim 5, wherein the solvent grade C3-C6 alcohol comprises greater than about 99.1 wt. % of a single C3-C6 alcohol.

7. The method of claim 1, wherein the stream is a portion of a fermentation broth.

8. The method of claim 1, further comprising:
conducting a bottom liquid produced in the rectification column to a distillation column to remove ethanol and produce a distilled bottom liquid; and
conducting the distilled bottom liquid to the step of separating a water-rich liquid phase from a C3-C6 alcohol-rich liquid phase.

9. The method of claim 1, further comprising sub-cooling a vapor distillate produced in the rectification column to recover a substantial portion of the vapor distillate and recycle the substantial portion of the vapor distillate to the recovery system.

10. The method of claim 1, wherein the method to recover the C3-C6 alcohol from the feed stream is conducted in a retrofit ethanol production plant, wherein the retrofit ethanol production plant comprised an ethanol recovery system, wherein the column in step (b) is a column from the ethanol recovery system.

11. The method of claim 10, wherein the column in step (b) is a first partition portion of a column from the ethanol recovery system.

12. The method of claim 10, wherein the recovery system further comprises a dehydration column.

13. The method of claim 10, wherein the column is a stripping column from the ethanol recovery system.

14. The method of claim 12, wherein the dehydration column is a retrofit rectification column of the ethanol recovery system.

15. The method of claim 11, wherein the recovery system further comprises a dehydration column and wherein the dehydration column is a second partition portion of the column from the ethanol recovery system.

16. The method of claim 10, wherein the method to recover a C3-C6 alcohol in the retrofit ethanol production plant does not require a molecular sieve.

17. The method of claim 10, wherein the method to recover a C3-C6 alcohol in the retrofit ethanol production plant does not use a molecular sieve.

18. The method of claim 1, wherein the C3-C6 alcohol is selected from the group consisting of propanol, butanol, pentanol, and hexanol.

19. The method of claim 18, wherein the C3-C6 alcohol is butanol.

20. The method of claim 19, wherein the butanol is selected from the group consisting of 1-butanol, 2-butanol, tert-butanol (2-methyl-2propanol), and isobutanol (2-methyl-1-propanol).

21. The method of claim 19, wherein the butanol is isobutanol (2-methyl-1-propanol).

* * * * *